US005516703A

United States Patent [19]

Caldwell et al.

[11] Patent Number: 5,516,703
[45] Date of Patent: May 14, 1996

[54] COATING OF HYDROPHOBIC SURFACES TO RENDER THEM PROTEIN RESISTANT WHILE PERMITTING COVALENT ATTACHMENT OF SPECIFIC LIGANDS

[75] Inventors: Karin M. E. Caldwell, Salt Lake County, Utah; Per J. E. Carlsson, Uppsala, Sweden; Jenq-Thun Li, Salt Lake City, Utah

[73] Assignee: The University of Utah, Salt Lake City, Utah

[21] Appl. No.: 110,169

[22] Filed: Aug. 20, 1993

[51] Int. Cl.⁶ .................. G01N 33/547; C07K 17/08; C12N 11/08
[52] U.S. Cl. .................. 436/532; 435/181; 436/531; 436/533; 436/823; 530/391.1; 530/816
[58] Field of Search .................. 436/533, 531, 436/532, 823; 435/181; 530/391.1, 816

[56] References Cited

U.S. PATENT DOCUMENTS

| | | | |
|---|---|---|---|
| 3,966,580 | 6/1976 | Janata et al. | 204/195 B |
| 4,048,416 | 9/1977 | Axén et al. | 526/9 |
| 4,149,003 | 4/1979 | Carlsson et al. | 546/261 |
| 4,179,337 | 12/1979 | Davis et al. | 435/181 |
| 4,264,766 | 4/1981 | Fisher | 536/51 |
| 4,711,951 | 12/1987 | Axén et al. | 530/323 |
| 5,006,333 | 4/1991 | Saifer et al. | 424/78 |
| 5,043,278 | 8/1991 | Hagaoka et al. | 435/181 |
| 5,219,926 | 6/1993 | Lindman et al. | 436/533 |
| 5,248,820 | 9/1993 | Sluka et al. | 435/531 |

OTHER PUBLICATIONS

J. Li et al. "Size Analysis . . . " ACS Symposium Series No. 472. Abstract, 1978.
Carlson et al., "Protein Thiolation . . . " Biochem J. 173, 723 (1978) Abstract, 1991.
F. Tiberg et al., Colloid Polym. Sci., vol. 270, pp. 1188–1193 (1992).
J. Lee et al., J. Biomed. Materials Research, vol. 23, pp. 351–368 (1989).
D. Kabakoff, Enzyme–immunoassay, Chapter 4, Chemical Aspects of Enzyme–Immunoassay, CRC Press, Inc. (1987).
S. Rudt et al., J. of Controlled Release, vol. 25, pp. 51–59 (1993).
C. Schroen et al., J. Membrane Science, vol. 80, pp. 265–274 (1993).
M. Brinkley, Bioconjugate Chem., vol. 3, pp. 2–13 (1992).

*Primary Examiner*—Mary E. Ceperley
*Attorney, Agent, or Firm*—James L. Sonntag

[57] ABSTRACT

A surface of specific reactivity is formed by adsorbing a modified block polymeric surfactant of the Pluronic-type, i.e., containing pendant poly(ethylene oxide) blocks attached at an end to poly(propylene oxide) center blocks and with specifically reactive groups at the unattached ends of the poly(ethylene oxide) blocks, upon a hydrophobic surface.

29 Claims, 2 Drawing Sheets

COATING OF HYDROPHOBIC SURFACES TO RENDER THEM PROTEIN RESISTANT WHILE PERMITTING COVALENT ATTACHMENT OF SPECIFIC LIGANDS

STATEMENT OF GOVERNMENT INTEREST

This invention was made with United States Government support under Grant No. 38003-04 awarded by the National Institutes of Health. The government has certain rights in this invention.

FIELD OF THE INVENTION

This invention relates to attachment of specific ligands on a hydrophobic surface.

BACKGROUND OF THE INVENTION

Hydrophobic surfaces, such as those of polystyrene, are nonspecifically active to the adsorption of various substances, such as biomolecules with hydrophobic portions, proteins, and the like. In an attempt to form specifically active surfaces, ligands which have specific reactivity have been covalently bonded to these surfaces. However, the covalent bonding to the surface is difficult to control, frequently resulting in splotchy coverage by the bonded ligand and several regions that are still nonspecific. Exemplary of methods used to immobilize a biomolecule upon a solid phase by covalent coupling are the coupling to agarose, crosslinked dextran or polyacrylamide or other hydrophilic polymers. Generally, functional groups on the solid substrate, such as hydroxide groups, are used to react with and covalently bind the molecule to be immobilized. A problem with these methods of immobilization is that they are not applicable to materials that lack such functional groups.

Another problem with covalently bound coatings, is that they, as a rule, are not removed from the substrate, which prevents recycling of the substrate. The porous polystyrene beads used in chromatography are expensive and after being coated are used for a specific separation and discarded when resolution is lost. It would be a significant cost savings if these beads could be stripped of the reactive coating and recycled by applying a new coating.

Certain biological molecules, such as enzymes and antibodies, can be immobilized by simple adsorption onto the solid phase. For example, an antibody may be adsorbed upon the surface of polystyrene in the form of a microliter plate, which is then used for heterogeneous enzyme immunoassay. The adsorbed biomolecule provides a specific enzymatic reaction or specific antibody-antigen interaction. Polystyrene is commonly used because of its transparency for colorimetric and photometric measurement, and because antibodies spontaneously bind to the polystyrene hydrophobic surface in a manner that usually preserves the immunochemical activity. However, it is necessary that essentially all of the hydrophobic sites on the surface be covered since they are non-specific adsorption sites. The background of the non-specific adsorption, if strong enough, can obscure the results of the assay. In addition, some biomolecules are difficult to adsorb upon polystyrene, and cannot be adsorbed to a sufficient extent for a practical assay. Others will only adsorb sufficiently under optimal conditions, which are often determined by trial and error. Further, some enzymes and antibodies lose activity when adsorbed upon a hydrophobic surface. For example, sensitive monoclonal antibodies sometimes lose activity due to conformational changes caused by the interaction with the hydrophobic surface. Therefore, the method of simple adsorption of active biomolecules upon a hydrophobic surface is not generally applicable.

It is known that certain block copolymers having a hydrophobic center block with hydrophilic end blocks can be used to coat hydrophobic surfaces. The center blocks are adsorbed onto the surface, with the end blocks extending from the surface and waving freely in a seaweed-like fashion. The coverage of the hydrophobic center blocks and the action of the end blocks effectively blocks the nonspecific adsorption sites and creates a nonadsorbing surface to certain substances such as proteins. A class of polymers commonly used in this application are the so-called Pluronic™ surfactants, which are triblock copolymers with the structure PEO—PPO—PEO (where "PEO" is poly(ethylene oxide) and "PPO" is poly(propylene oxide). Polymers of this type are also available under the name Poloxamer™. In a specific application, Pluronic surfactants have been found to reduce the platelet adhesion and protein adsorption on surface treated glass or low density polyethylene. Pluronic surfactants have also been found to prevent bacterial adhesion on polystyrene surfaces. While a Pluronic coating essentially eliminates the non-specific reactivity of the substrate surface, the resulting hydrophilic surface has essentially no reactivity and is not a suitable surface for further adsorption of most biomolecules.

Many techniques for biochemical separation, such as low pressure affinity chromatography and immunological assays, are based on specific interactions between biomolecules of examination and chemical reagents immobilized on solid phase. However, because of the above difficulties encountered with covalently bound coatings and adsorbed coatings of reactive ligands, there is a need of a coating system that is generally applicable for different reactive ligands, has a higher degree of reactivity, and has little or no background non-specific reactivity.

Another aspect of biochemical separations are those based upon specific interaction between biomolecules to be examined and chemical reagents immobilized upon a solid phase. Such separations are the basis for, for example, low pressure affinity chromatography and solid phase immune assays.

SUMMARY OF THE PRIOR ART

U.S. Pat. No. 4,264,766 to Fisher discloses a water-insoluble immunological-reagent formed by covalently binding discrete particles of a water insoluble latex carrier and a water-soluble polyhydroxy compound. The latex carder has active groups that can form a covalent linkage with a polyhydroxy compound. The polyhydroxy compound has at least two hydroxyl groups and is capable of rendering the surface of the latex carrier hydrophilic and suitable for covalent attachment of immunologically active materials, e.g., myoglobin.

U.S. Pat. No. 5,006,333 to Saifer et at. discloses a biologically persistent, water-soluble, substantially non-immunogenic, substantially non-antigenic conjugate of superoxide dismutase prepared by coupling at least a portion of the superoxide dismutase amino, carboxyl, or sulfhydryl groups to polyalkylene glycol.

U.S. Pat. No. 5,043,278 to Nagaoka et al. discloses a fixing material for use with physiologically active substances comprising a water insoluble carrier, an alkylene oxide chain bonded at one end to the carder with a functional group at the nonbonded end capable of reacting with a physiologically active substance.

U.S. Pat. No. 3,966,580 to Janata et al., discloses a protein-immobilizing hydrophobic polymeric membrane comprising (a) an organic hydrophobic polymeric substrate swellable by a solvent, (b) a hydrocarbon chain partially absorbed into the surface with a reactive site reactive with one compound of an immunochemically reactive pair attached to the nonabsorbed portion, and (c) one member of an immunochemically reactive pair reacted with the reactive site. The result is a hydrophobic substrate with a preselected concentration of protein reactive groups pendant therefrom. The concentration of the protein reactive sites is sufficiently low such that the polymeric substrate retains its hydrophobic character. The hydrophobic polymeric membrane is prepared by forming a thin membrane of hydrophobic polymer that contains no pendant polar groups, e.g., poly(vinyl chloride), polystyrene. The polymeric membrane is then reacted with a solvent that can swell the membrane. The solvent contains an aliphatic compound with a reactive site, preferably at or near one end of the carbon chain. After the membrane has been swollen with the solvent, the polymeric membrane is dried without removing the aliphatic compound with reactive sites. After the membrane is dried, it is reacted with a compound with a protein-reactive site and a site reactive with the reactive site on the aliphatic compound. The membrane surface is then washed and placed in a solution containing the protein to be immobilized.

OBJECTS OF THE INVENTION

It is, therefore, an object of the invention to provide a coating for a hydrophobic substrate that provides the surface with specifically reactive sites at a predetermined concentration.

It is also an object of the invention to provide a hydrophilic protein compatible coating for hydrophobic substrates with little or no background nonspecific reactivity.

Further objects of the invention will become evident in the description below.

SUMMARY OF THE INVENTION

In the present invention, the ends of block surfactant polymers with hydrophilic pendant blocks attached to a hydrophobic block are reacted to form a derivative of the surfactant polymer with specifically active sites at the free ends of the hydrophilic blocks. The derivative is then adsorbed onto the hydrophobic substrate to produce a surface with a minimum of nonspecific activity from the hydrophobic substrate and with specific activity provided by the block copolymer derivative.

The derivative surfactant polymer may be diluted with unmodified polymer before coating on the surface. In this way, it is possible to predetermine the concentration of the active sites on the surface, which are evenly distributed on the surface. Thus, the surface may be made specific not only to certain chemical entities, but also to size by the spacing of the reactive sites. In addition, mixed functionality may be achieved by mixing different block copolymer derivatives. Both unmodified and modified block surfactant polymers adsorb upon a hydrophobic polymer substrate quickly (within minutes or hours) in an aqueous environment. The terminal substituents on the ends of modified block copolymers appear to have little effect on these adsorption properties. Accordingly, the proportion of active sites on the surface is essentially directly proportional with the fraction the modified surfactant polymer in the mixture.

In the preferred embodiment, the reactive group on the modified surfactant polymer includes a group that can participate in a rapid specific thiol exchange with a thiol-containing protein. The surface resulting from the modified polymer adsorbed on the hydrophobic substrate is hydrophilic and quite compatible with proteins that can be immobilized on the surface through the reactive sites. Accordingly, reactivation of the adsorbed protein is minimized as there is little surface and conformational effects resulting from the immobilization.

Compared to the prior-art surfaces formed by covalent linking or simple adsorption, the specific reactive surfaces of the invention are relatively easy to form and typically constitute surfaces with greater specificity and lower background reactivity. Unlike prior-art covalently linked surfaces, with the present invention the reactive coating can be stripped from the hydrophobic substrate and the substrate recycled. This represents a significant savings in chromatographic applications where the polymer beads used are expensive and have been discarded after a loss of activity because the covalently linked surfaces cannot be easily removed. Compared to surfaces wherein a protein has been simply adsorbed on the surface, the surfaces provided by the coatings of the invention have a higher specific reactivity per unit area of surface with an even distribution of reactivity. In addition, there is little or no background nonspecific reactivity resulting from adsorption to unshielded surfaces.

An embodiment of the invention is a hydrophilic surface with a specific chemical reactivity comprising;

(a) a hydrophobic polymer substrate, (b) a modified polymeric surfactant adsorbed upon the surface of the substrate, the modified polymeric surfactant having pendant hydrophilic blocks with one end attached to a hydrophobic block and the other end attached to pendant reactive groups, said reactive groups being stable in water and providing the specific chemical reactivity to the surface.

Another embodiment of the invention comprises a method for forming a hydrophilic surface on a hydrophobic substrate with a specific chemical reactivity, which method comprises;

(a) providing a hydrophobic polymer substrate, (b) adsorbing upon the substrate surface a modified polymeric surfactant, the modified polymeric surfactant having pendant hydrophilic blocks with one end attached to a hydrophobic center block and the other end attached to pendant reactive groups, said reactive groups providing the specific chemical reactivity to the surface.

The modified polymeric surfactant is a derivative of a polymeric block copolymer with pendant or dangling poly(ethylene oxide) (PEO) chains with a —OH group on one end and attached at the other end to a poly(propylene oxide) (PPO) chain. The polymeric block copolymer may be in the form of any arrangement of the PEO and PPO blocks with the general formula;

$$(HO-PEO)_a(PPO)_b \tag{1}$$

where a and b are integers, are the same or different and are at least 1, preferably a is between 1 and 6, and b is between 1 and 3, more preferably a is 1 to 2, and b is 1. The polymeric block copolymer has a PEO (—C$_2$H$_4$—O—) content between 10 wt % and 80 wt%, preferably 50 wt % and 80 wt %, more preferably between 70 wt % and 80 wt %.

The PEO chains or blocks are of the general formula;

$$-(-C_2H_4-O-)_u- \tag{2}$$

where u is the same or different for different PEO blocks in the molecule. Typically, u is greater than 50, preferably between 50 and 150, more preferably between 80 and 130. The PPO blocks are of the general formula;

 (3)

where v may be the same or different for different PPO blocks in the molecule. Typically, v is greater than 25, preferably between 25 and 75, more preferably between 30 and 60.

The block copolymers may be branched structures and include other structures (e.g. bridging structures, or branching structures) and substituents that do not materially affect the ability of the block copolymer to adsorb upon and cover a hydrophobic surface. Examples include the following polymeric surfactants described in the following paragraphs.

Preferably, the modified polymeric surfactant of the invention is a derivative of a polymeric tri-block copolymer with pendant —OH groups, as in Formula (4), below. These tri-block copolymers have a hydrophobic center block of polypropylene oxide and hydrophilic end blocks of polyethylene oxide with terminal —OH groups, and can be represented by the formula;

HO—(—C$_2$H$_4$—O—)$_x$—(—C$_3$H$_6$—O—)$_y$—(—C$_2$H$_4$—O—)$_z$—H (4)

where y is between 25 and 75, preferably between 30 and 60, and x and z are preferably the same, but may be different, and are between 50 and 150, preferably 80 and 130. Certain of these polymeric surfactants are commercially referred to as "Pluronic™" or "Poloxamers™", and are available, for example, from BASF.

Another suitable class of polymeric block copolymers is the di-block copolymers where a=1 and b=1, and can be represented by the formula;

HO—PEO—PPO—H (5).

where PEO and PPO are defined above.

Another suitable class of polymeric block copolymers is represented by the commercially available Tetronic™ surfactants (from BSAF), which are represented by the formula;

(H—(O—C$_2$H$_4$)$_u$—(O—C$_3$H$_6$)$_v$)$_2$N—CH$_2$—CH$_2$—N((—C$_3$H$_6$—O—)$_v$—(—C$_2$H$_4$—O—)$_u$—H)$_2$ (6)

As used herein, the terms "Pluronic" or "Pluronics" refer to the block copolymers defined in Equation (1), which include the Pluronics™ tri-block copolymer surfactants, the di-block surfactants, the Tetronic™ surfactants, as well as other block copolymer surfactants as defined.

The —OH end groups of the PEO chains of the polymeric surfactant are modified to introduce a small reactive organic group which is stable in water. When the modified polymeric surfactant is adsorbed in an aqueous environment upon a hydrophobic substrate, the reactive groups impart specific reactivity to the surface. Using the Pluronics represented by equation (4) as an example, if both —OH groups on the pendant PEO chains are substituted, the modified surfactant has the formula;

R—O—(—C$_2$H$_4$—O—)$_x$—(—C$_3$H$_6$—O—)$_y$—(—C$_2$H$_4$—O—)$_z$—R (7)

where R is a reactive group. Accordingly, the general formula for the modified polymeric surfactants of the invention is;

(HO—PEO)$_c$(R—O—PEO)$_d$(PPO)$_b$ (8)

where c+d is equal to a in formula (1), and c is 0 or a positive integer, and b is defined above for formula (1). The R group may be any reactive group that is stable in water and will impart the desired selective reactivity for the substrate surface when the modified surfactant is adsorbed upon the surface. The specific reactivity may be to any non-water entity or entities. By "non-water entity" is meant an entity that is not water.

The R group must be stable in an aqueous environment, as adsorption of the modified polymeric surfactant upon a hydrophobic surface requires an aqueous environment. The R group may, for example, contain a member of the group consisting of —NH$_2$, —SH, —SO$_3$—, —NHNH$_2$, —COOH, and maleimide. As an example, the R group may impart reactivity for conjugating other functional groups or for radioisotope labelling. The reactive group may be further modified and conjugated with other functional groups to form a different R group. In this manner a reactive group can be provided, such that after adsorption of the modified polymer surfactant upon the surface a reactive specific surface is formed, for example, for the immobilization of proteins. The R groups are chosen such that they do not significantly impair adsorption of the modified polymeric surfactant on the hydrophobic surface.

In a preferred embodiment of the invention, the reactive R group contains a hydrazino group (by further reacting a p-nitrophenyl group), a thiopyridyl group, a tyrosyl residue, or a maleimide.

In a preferred embodiment the R group is for the immobilization of protein or polypeptide molecules and contains the structure;

—S—S—R″ (9)

where R″ is selected from the group consisting of (1) 2-benzothiazolyl, (2) 5-nitro-2-pyridyl, (3) 2-pyridyl, (4) 4-pyridyl, (5) 5-carboxy-2-pyridyl, and (6) the N-oxides of any of (2) to (5). The reactivity of these groups with proteins and polypeptides is discussed in U.S. Pat. No. 4,149,003 to Cadsson et al. and U.S. Pat. No. 4,711,951 to Axén et al.

In the present invention R may be, but is not limited to, a member of the group consisting of hydrozino, thiopyridyl, tyrosyl, maleimide, 2-pyridyl disulphide, 5-nitro-2-pyridyl disulphide, 4-pyridyl disulphide, 5-carboxy-2-pyridyl disulphide, and the nitrogen oxides of 2-pyridyl disulphide, 5-nitro-2-pyridyl disulphide, 4-pyridyl disulphide, and 5-carboxy-2-pyridyl disulphide.

R may also be;

 (10)

or

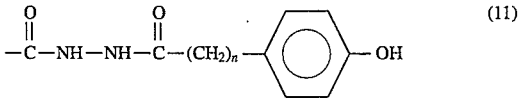 (11)

wherein n is between 1 and 4, or R may be chosen from the group consisting of;

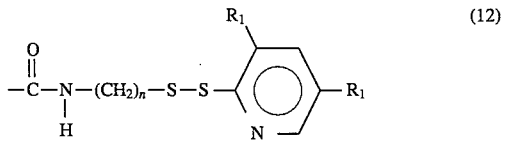 (12)

-continued

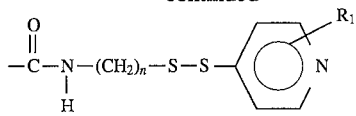
(13)

wherein n is greater than 1, preferably between 1 and 4, and $R_1$ is —$NO_2$ or —H.

R may also be;

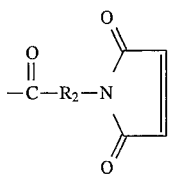
(14)

where $R_2$ is —$(CH_2)_n$—, a phenyl group or a cyclohexyl group, and n is greater than 1, preferably between 1 and 4.

The modified polymeric surfactant is adsorbed upon a hydrophobic polymer substrate to provide a surface with specific reactivity. The hydrophobic polymer substrate comprises any suitable polymer which imparts a hydrophobic character to the surface of the substrate. By "hydrophobic" is meant that the surface has a water contact angle greater than about 60°, preferably greater than about 70°. Suitable polymers with surfaces having a water contact angle greater than 70° include, but are not limited to polystyrene (PS), polymethylmethacrylate (PMMA), polyolefins (e.g. polyethylene (PE), polypropylene (PP)), polyvinylchloride (PVC), silicones, and block copolymers containing these constituents.

The less hydrophobic polymer substrates (water contact angle between 60° and 70°), such as PVAc are also contemplated by the invention but are less preferred. Adsorption upon these polymers would be expected to be less than for more hydrophobic polymers such as PS and PMMA, and slow release of the surfactant from the polymer surface over time would be expected. Hydrophilic substrates such as silica, agarose, and polyvinyl alcohol are not contemplated by the present invention. However, it is contemplated that hydrophilic substrates may be treated to render them hydrophobic before adsorption thereon of the modified polymeric surfactant. For example, silica can be treated with dimethyldichloro silane to provide a hydrophobic surface.

The polymer may be porous or nonporous, or be in the form a flat surface (e.g. a microtiter plate), or any suitable shape, such as micro beads, and the like used in chromatography applications. The polymeric surfactant may also be adsorbed upon colloidal or latex particles of a suitable hydrophobic polymer.

The modified polymeric surfactant adsorbs with the PPO blocks upon the hydrophobic surface and the pendant PEO blocks dangling away from the surface into the aqueous surroundings. Using a triblock copolymer as an example, the adsorbed surface can be illustrated by the formula below;

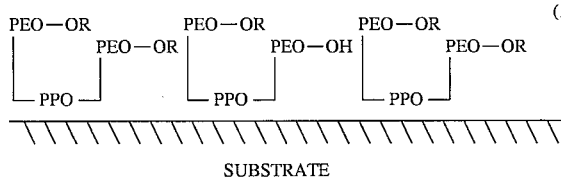
(10)

In order to yield the desired number of reactive groups per unit area of surface, the modified polymeric surfactant may be mixed with unmodified polymeric surfactant and the mixture adsorbed upon the surface.

The modified surfactant polymer adsorbed upon the surface provides a much lower background of non-specific reactivity than the surface itself. In the prior-art, such as where moieties with specific reactivity are covalently bound to the hydrophobic surface, significant areas of the surface are left uncovered that have nonspecific reactivity. This can result, for example, from an uneven and incomplete distribution over the hydrophobic surface of the reactive moieties, leaving nonspecific reactive sites on the hydrophobic surface.

By practice of the invention, the structure of the adsorbed polymer, with the hydrophobic PPO portion adsorbed upon the surface and the hydrophilic PEO pendent blocks extending in a "sea-weed" fashion from the surface effectively blocks protein adsorption upon the surface. The reactive end groups on the modified surfactant polymer, therefore, provide essentially the only reactivity for the surface, which reactivity can be easily predetermined by choice of the reactive end group.

The means of providing the reactive R groups is by substituting the PEO end —OH groups of the Pluronic with a suitable —O—R group. This may be accomplished by adapting any known method or combination of methods for synthesizing poly(ethylene glycol) derivatives wherein pendant —OH groups are substituted to form —O—R groups that are stable in an aqueous environment.

In a preferred embodiment of the invention, the Pluronic is first modified in an organic solvent to introduce 4-nitrophenyl-carbonate groups by treatment of Pluronic with 4-nitrophenyl chloroformate. This forms an intermediate of the Pluronic which has a reactive group (R') that is not stable in an aqueous environment but is suitable for binding of various reactive groups, R, which are in turn stable in an aqueous environment. This embodiment is exemplified in Example 1.

An intermediate Pluronic that is not water-stable, but has suitably reactive R' groups for binding of water-stable R groups, may have a reactive R' that is, for example, n-hydroxysuccinimide or similar electrophilic structure, or p-nitrophenyl. In an embodiment of the invention, R' is chosen from the group disuccinimidyl carbonate generated esters or tosylchloride generated esters (as, for example, in Formulas (11)and (12), respectively).

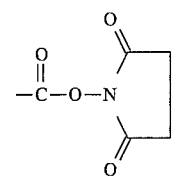
(11)

(12)

Any intermediate R' group, whether water-stable or not water-stable are contemplated by the invention if they can be further reacted to produce the water-stable R groups herein described. The R' groups which are not water-stable, but are stable in organic solvents, are bound to the block copolymers by suitable reaction with the —OH pendant groups on the PEO chains in organic solvents.

Preferably, the water-stable reactive organic groups, R, include a thiopyridyl group. The resulting thiopyridyl-modified Pluronic may then be used to bind a thiol containing protein. Since most proteins are either naturally thiol-containing or can be easily thiolated, this embodiment is applicable for most biomolecules of interest. An exemplary use of this embodiment is as an improved ELISA (enzyme linked immunosorbent assay). In an ELISA application of the invention, the surface adsorbed thiopyridyl-modified polymeric surfactant is bound with, for example, a thiolated anti-IgE antibody. In comparative tests to determine the amount of IgE antigen that binds to the attached antibody, it was found that amount of bound antigen per unit area was significantly higher for the invention than for a conventional ELISA method, wherein the antibody itself is allowed to adsorb passively upon a hydrophobic surface. This demonstrates a stronger response to the antigen for the ELISA of the invention than for the conventional ELISA.

In another embodiment of the invention, the reactive end groups, R, include a radioactive species, e.g., $^{125}$I, or a group to which a radioactive species may be attached. This embodiment permits further study and direct quantification of the adsorption of the polymer surfactant upon the either a flat surface or on colloidal particles.

The present invention provides an improved means for immobilizing biomolecules upon a hydrophobic surface, by derivatizing the Pluronic surfactants with reactive groups that are reactive with the biopolymer to be immobilized. The modified Pluronic is adsorbed upon the hydrophobic surface, and because of the PPO/PEO block structure of the Pluronic, essentially all of the hydrophobic sites on the polymer surface are immobilized (either covered by the PPO blocks or "guarded" by the waving pendent PEO blocks). The biomolecule to be immobilized is then linked to this surface which is made specifically reactive due to reactive PEO-block end groups of the surfactant extending from the surface. Thus, the surface is highly specific in reactivity, and there is little or no residual activity from the hydrophobic surface of the polymer substrate. The surface provided by the adsorbed modified Pluronic molecules is also compatible with the adsorbed, immobilized molecules and will not affect activity to the degree of a plain hydrophobic surface.

By employing a reaction of hydroxide ends of Pluronic surfactants with 4-nitrophenyl chloroformate, one can efficiently introduce reactive carbonate groups to such PEO/PPO block copolymers. These activated Pluronics are very stable in organic milieu and in a dry state and hydrolyze readily in water. Since they react relatively easily in an organic solvent with amino groups, 2-pyridyl disulfides, peptide, hydrazino and other amino containing chemicals can be thus conjugated to the Pluronics. Using hydrazino groups as the bridge, tyrosyl groups for radioisotope labelling purpose can be subsequently coupled to the Pluronic by a reaction with the Bolton-Hunter reagent.

Based on the specific thiol-disulfide reaction and the surfactant properties of Pluronics, hydrophobic surfaces coated with the 2-pyridyl disulfides conjugated Pluronic provide a new way to have hydrophobic surfaces become much more protein compatible and at the same time to immobilize desired molecules under a certain control. The rate of hydrolysis of the 2-pyridyl disulfides groups at pH~8.5 is almost negligible in comparison with the rate of the thiol-disulfide exchange reaction, and such a surface coating can be sensitively activated at very low concentration of thiol-containing biomolecules such as proteins. The coupling releases thiopyridone; its release constitutes a sensitive method for detecting the degree of substitution (exchange), since the thiopyridone can be readily and accurately quantified by spectroscopic detection at 343 nm with an extinction coefficient of $8060/cm^{-1}M^{-1}$. Since the thiol-disulfide exchange is a reversible reaction, the bound molecules can be therefore released from the solid phase by adding small molecular weight of thiol-containing reagents. Thiol groups can be substituted to biomolecules without inactivation by a number of general methods, and the solid phase can be a hydrophobic surface in the form of particles (porous or nonporous) or small plates. This surface coating technique is, therefore, a very general and valuable method for the use in chromatography, enzyme immobilization, and solid-phase immunoassays, and is particularly attractive compared to the direct covalent immobilization techniques, which are complicated and expensive.

DETAILED DESCRIPTION OF THE INVENTION

Figure 1:
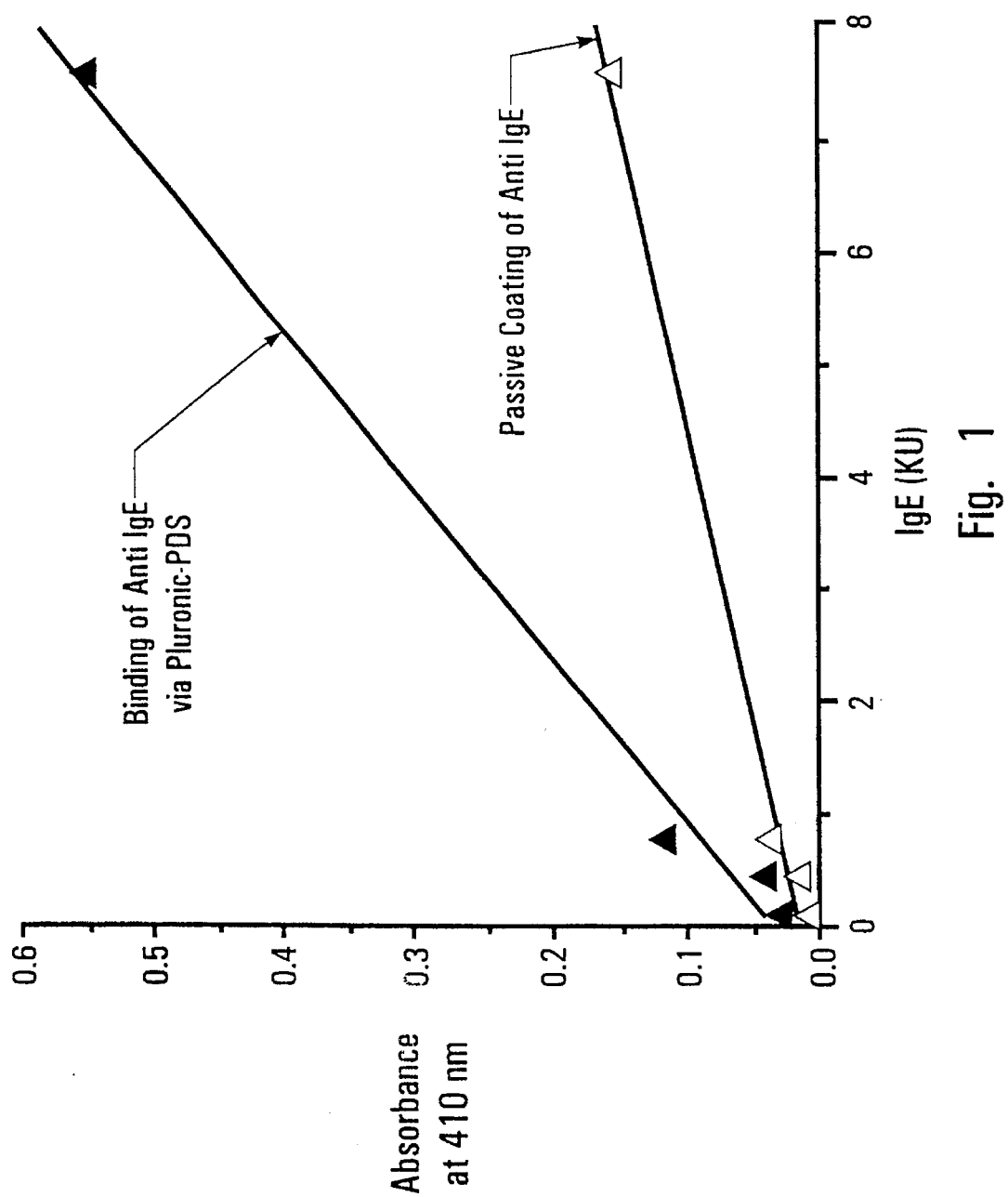
FIG. 1 is a graph showing activity of anti IgE immobilized on a coated surface of the invention compared with a surface of the prior-art.

In the examples below, the following materials were used;

Pluronic surfactants—P105, F68, F88 and F108, available from BSAF. Each have the formula as in (9) above where x and y are shown in Table A, and z is the same as x;

TABLE A

| Pluronic Surfactants | | |
|---|---|---|
| | x | y |
| P105 | 37 | 56 |
| F68 | 76 | 30 |
| F88 | 104 | 39 |
| F108 | 129 | 56 |

The molecular weight of Pluronic surfactants P105, F68, F88, and F108, are 6500, 8400, 11400, 14600. P 105 comprises 50 wt. % PEO whereas F68, F88, and F108 consist of about 80 wt. % PEO. All were available from BASF under the tradename Pluronic™.

Polystyrene (PS) beads (10 μm diameter). Available from Pharmacia-BTG-LKB, Uppsala, Sweden.

4-nitrophenyl chloroformate. Available from Aldrich.

Hydrazine. Available from EM Science

Triethylamine (TEA). Available from Baker.

Bolton-Hunter reagent. Available from Pierce.

Chloramine-T. Available from Eastman Kodak.

Na$^{125}$I (100 mCi/ml). Available from Amersham.

Sodium metabisulphite. Available from Fisher.

Dithiothreitol (DTT). Available from Bio-Rad.

Mercaptoethylamine hydrochloride, 2,2'-dithiopyridine, and β-galactosidase (Grade 8 from *E. Coli*). All available from Sigma.

PD-10 containing Sephadex G-25M columns from Pharmacia, and dialysis membranes (Spectra/Por) available from Spectrum Medical.

PBS—phosphate buffered saline.

EXAMPLE 1

Activation of Pluronic with 4-Nitrophenyl Chloroformate

Pluronic surfactants P105, F68, F88, and F108 were modified according to the invention. 2 g of Pluronic was first dissolved in 6 ml benzene and then this solution was slowly added to stirred solution of 4-nitrophenyl chloroformate in 6 ml benzene. The content of 4-nitrophenyl chloroformate varied with the molecular weight of the Pluronic used but the ratio of —OH:-nitrophenyl for the reaction was kept at 1:3. After 24 hours of shaking, the reaction activated product was precipitated at least twice using ether and was recovered by filtration followed by evaporative removal of the remaining solvent under vacuum overnight. For Pluronic P105, the precipitation was done by using 80 times excess petroleum ether (bp 35°~60° C.). The degree of substitution was determined by measuring the released para-nitrophenolate ions in an alkaline solution using a spectrophotometer. This is shown below for Pluronic F108, where "F108—OH" represents a Pluronic F108 block molecule and one of its pendent —OH groups.

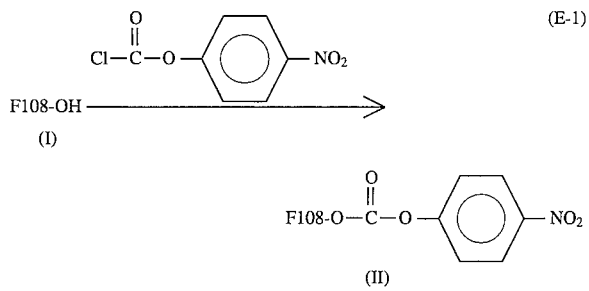

After 1 hour under rotation, the absorbance was measured. An accurately weighed out sample of 4-nitrophenyl chloroformate activated Pluronic derivative was dissolved in 0.1M NaOH and measured at 402 nm using a molar extinction coefficient of 18400 cm$^{-1}$M$^{-1}$.

From the measure of released yellow para-nitrophenolate ions in an alkaline solution, the degree of substitution was calculated by assuming two available —OH groups in each Pluronic molecule. The results are summarized in Table B, and show a degree of substitution around 80%.

TABLE B

| 4-Nitrophenyl Chloroformate Modification of Pluronic Surfactants | |
|---|---|
| | Degree of Substitution (%) |
| Pluronic P105 | 82 |
| Pluronic F68 | 78 |
| Pluronic F88 | 85 |
| Pluronic F108 | 83 |

The substitution rate of each Pluronic which was reported as the average value of at least three repeated experiments the same ratio —OH:-nitrophenyl of about 1:3. The substitution did not significantly increased when a larger excess of reagent was used. The activated Pluronic surfactants were stably stored in desiccator over P$_2$O$_5$ at room temperature, and were not found to loose activity after months of storage.

The conjugation of para-nitrophenyl-carbonate groups to the PEO ends of Pluronic was found to be an efficient coupling chemistry and the substitution was essentially independent of the chemical composition of the Pluronic surfactant. Although the reactive end group of the modified Pluronic (II) is not stable is water and, therefore, the modified Pluronic cannot be adsorbed upon a surface in an aqueous environment with retained activity, it provides a useful intermediate for formation of other reactive end groups that are stable in water.

EXAMPLE 2

Radioisotope $^{125}$I Labelling of Pluronic

A. Reaction with Hydrazine 1.5 g of activated Pluronic product (II) produced as in Example 1 was dissolved in 3 ml methanol and was mixed with 97% hydrazine. The molar ratio of hydrazine to Pluronic was kept as 100:1. After 8 hours reaction, precipitation using ether was repeated at least twice and the final product was dried under vacuum overnight. The reaction was as follows, using activated Pluronic F108 as illustration;

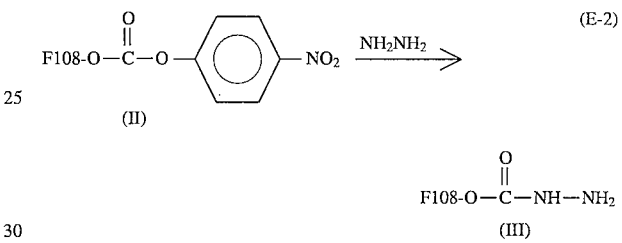

For Pluronic P105, the recovery of the product was by a dialysis process. The mixture after reaction was concentrated in a rotator vaporizer for 1~1.5 hours and was then dissolved in 6 ml methanol. This solution was then transferred to a dialysis bag with molecular weight cut off of 1000 Daltons and was dialyzed against a 30% aqueous methanol solution. This methanol/water mixture (500 ml) was changed three times in 24 hours, and then replaced by 0.1M NaHCO$_3$ solution (500 ml). This weak alkaline solution was changed every 8 hours, and was continued 3~4 times until essentially all nitrophenol was completely removed. Then, deionized water was used as the incubation solution and was changed three times in 24 hours. The product (III) was then recovered by lyophilization. The hydrazine-modified Pluronic (III) is stable in water and provides a useful intermediate for formation of other water-stable modified polymeric surfactants that can be adsorbed upon a surface in an aqueous environment.

B. Reaction with Bolton-Hunter reagent

The Bolton-Hunter reagent is an efficient chemical for coupling to —NH$_2$ groups for subsequent labelling with radioisotope $^{125}$I. Bolton-Hunter reagent was conjugated with the hydrazine reacted product above (III) by mixing vigorously 1 volume of a 17 mM solution of product (III) in dimethyl sulfoxide with 4 volumes of a 43 mM Bolton-Hunter reagent in dimethyl sulfoxide. After 4 hours, the product was precipitated from the solution using ether, and then dried under vacuum overnight. The reaction for the F 108 derivative is shown below for illustration;

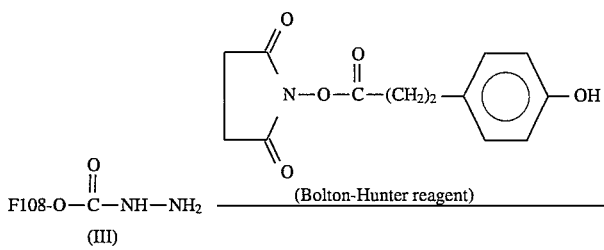

(E-3)

For Pluronic P105, tetrahydrofuran instead of dimethyl sulfoxide was used as the solvent. After 4 hours reaction, this mixture was concentrated in a rotator vaporizer and then was dissolved in 3 ml methanol. This solution was then transferred to a dialysis bag with a molecular weight cut off of 1000 Daltons and was dialyzed against methanol for 8 hours, and then against deionized water for 8 hours. The incubation solution was then replaced by fresh deionized water and after 8 hours the product was sent to lyophilization to determine (IV). The substitution rate of such reagent can be calculated from measurements of the amount of conjugated tyrosyl groups in each Pluronic molecule. The degree of substitution is shown below in Table C;

TABLE C

| Bolton-Hunter Modification of Pluronic Surfactants | |
|---|---|
| | Degree of Substitution (%) |
| Pluronic P105 | 64 |
| Pluronic F68 | 84 |
| Pluronic F88 | 93 |
| Pluronic F108 | 93 |

A series of Bolton-Hunter reagent in samples with various concentrations were prepared in methanol and the UV absorptivity were determined at a wavelength of 270 nm using a Perkin-Elmer Lambda 6/PECSS spectrophotometer. From these measurements a molar extinction coefficient of such a tyrosyl group was calibrated as $1270\ cm^{-1}M^{-1}$. Finally, 0.5 ml of 0.6 mg/ml of product (IV) in PBS buffer (0.15 M, pH=7.4) was treated with 3 μL of $Na^{125}I$ and 50 μL of 4 mg/ml chloramine-T was added as oxidizing reagent. This ionization reaction was terminated after 4 hours by using 50 μL of 4.8 mg/ml sodium metabisulphite. The reaction to produce the iodated product (V) is shown as follows for F 108;

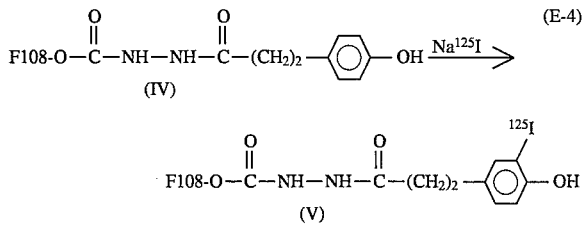

The labelled polymers were separated from free $Na^{125}I$ by using a PD-10 column. To test the stability of the isotope labelled F-108 on a substrate, PS latex particles with product (V) adsorbed to their surface were suspended in a surfactant free buffer for 3 days and measurements showed no loss of surfactant from the surface.

The radioactive labelling of the Pluronic surfactant is useful for quantitative studies. In general, it is very difficult to quantify the Pluronic precisely because it has no functional groups which can be specifically determined by a common instrument. Although the turbidity measurement of Pluronic is the most common technique for this purpose, this method usually has many limitation and is usually available only for polymers in a dust-free solution. By introduction of tyrosyl groups onto the para-nitrophenyl-carbonate activated Pluronic molecules followed by iodination of such functional groups, the Pluronic molecules have been found to be easily labelled with radioactive iodine. The Bolton-Hunter reagent with a succinimidyl and a tyrosyl group is a good reagent for coupling with —$NH_2$ groups in proteins, and such conjugated biological molecules can subsequently be labeled with high specific radioactivities. This method is applied to Pluronics by first providing available —$NH_2$ groups on the Pluronic molecule. This was accomplished by substituting the hydrazino groups to the Pluronics by the reaction of hydrazine and para-nitrophenyl-carbonate activated Pluronics. This reaction usually went close to completion and the measure of released para-nitrophenol was in good agreement with the quantification of product (IV). High substitution rate indicated that the reaction of the hydroxyl succinimide ester of the Bolton-Hunter reagent and —$NH_2$ groups in modified Pluronic is also a very efficient chemistry.

The purified tyrosyl conjugated Pluronic was then ready for the radioactive iodine labelling. Following treatment with chloramine-T and $Na^{125}I$, the $^{125}I$ labelled Pluronic and free $Na^{125}I$ were separated by passing through a PD-10 column, and the eluants were separated into 12 culture tubes. 20 μl of each 1 ml fraction of the eluant was transferred into a counting vial and the radioactivity was counted by a radioisotope detector (Beckman 170M). The GPC profile showed that the labelled Pluronic F108 was flushed out as the void, and the small molecular weight $Na^{125}I$ in the column and eluted out later. The radioisotope labelled polymers were collected and passed through column again to check the distribution of free $Na^{125}I$ in the solution. Following the same counting procedure as before, no $Na^{125}I$ was detected. The elution patterns for other Bolton-Hunter conjugated Pluronics that were tested were all similar. The labelling efficiency estimated by observing the second GPC profile was around 95~96%.

In the above reaction system, Pluronic F68, F88 and F108 were all modified chemically in organic solvents and were successfully recovered by ether. The yield for each step was from 75% to 80%. However, P105 can not be likewise separated from nonreacted reagents and was often recovered by other elaborate procedures. This solubility difference in ether may result from the different chemical composition between P105 and other selected Pluronics because P105 contains only 50% PEO whereas other samples of Pluronics derivitized in these examples contain 80% PEO. In order to provide an efficient way to recover P105 in a general chemical reaction, we have tested its solubility in different solvents. It was found that P 105 can be easily dissolved in aqueous media and in most organic solvents including benzene, pyridine, chloroform, methanol, tetrahydrofuran, dimethyl sulfoxide, etc., and can be only precipitated well by 80 times volume excess of petroleum ether in such solvents except in methanol and dimethyl sulfoxide. In addition to the finding that the released para-nitrophenol during the hydrazine reaction was not dissolved well in petroleum ether, the yield of the dialysis and lyophilization method to purify the hydrazino and tyrosyl substituted P 105 was generally comparable to the precipitation methods by ether.

EXAMPLE 3

Preparation of Pluronic-2-Pyridyl Disulfide Derivative

A product (II) as in Example 1 was prepared using Pluronic F108. 2-(2-pyridyl dithio)ethylamine was then prepared for conjugating pyridyl disulfide group to Pluronic F108, according to the reaction below.

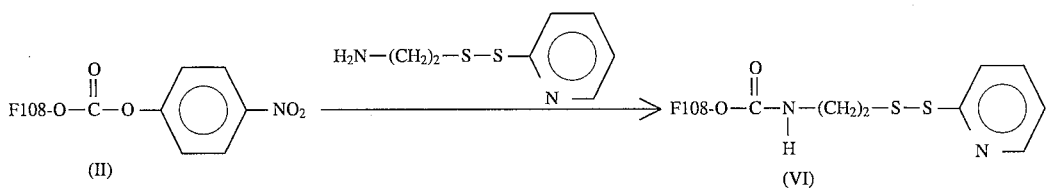

In this step, the 2-(2-pyridyl dithio)ethylamine hydrochloride was first prepared by dissolving 1.13 g mercaptoethylamine hydrochloride into 2 ml methanol containing 0.8 ml acetic acid, which was then added dropwise to a stirred solution of 6.74 g 2,2'-dithio pyridine. The yellow reaction mixture was stirred for 30 minutes at room temperature and was then slowly poured into a beaker with 200 ml stirred ether. The product that was separated from the ether was dissolved in a small volume of methanol and was again precipitated with ether. This procedure was repeated until the crystal appeared white and then the product was recovered by evaporating the ether under vacuum. 2-(2-pyridyl dithio)ethylamine hydrochloride (0.6 g) was dissolved in 3 ml methanol and converted to 2-(2-pyridyl dithio)ethylamine after the addition of 300 mg of TEA.

1 g 4-nitrophenyl chloroformate activated F108 pluronic (II) was dissolved in 3 ml methanol and added to the above-stirred 2-(2-pyridyl dithio)ethylamine solution. The reaction mixture which immediately turned yellow was left at room temperature for 15~20 hours. The TEA was then neutralized by adding 2~2.5 ml 10M HCl. Deionized water (4 ml) was added to this mixture and this solution was transferred to a dialysis tubing (with a molecular weight cut off of 3,500 Daltons) and was dialyzed against 4 liter deionized water. During the 48-hour dialysis process, water was changed five times until the low molecular weight material was believed to be completely removed. The F108-2-pyridyl disulfide derivative (F108-PDS) (VI) was finally recovered by lyophilization. The derivative (VI) was stored in a desiccator over $P_2O_5$ at room temp. The determination of the content of 2-pyridyl disulfide groups was carried out essentially as described in Carlsson et al. "Protein Thiolation and Reversible Protein-Protein Conjugation, N-Succinimidyl 3-(2-pydridyldithio)propionate, a New Heterobifuncional reagent," *Biochem. J.*, 173,723 (1978). Exactly weighed F108-PDS was dissolved in phosphate-NaCl buffer (0.2M, pH 7.3). The UV absorbance at wavelength 343 nm was measured before and 10 minutes after addition of 0.1 ml of 25 mM DTT to both reference cuvette containing buffer and sample cuvette containing F108-PDS. The concentration of released 2-thiopyridone which is identical to the original concentration of F108-PDS was calculated using a molar extinction coefficient of 8060 $cm^{-1}M^{-1}$

EXAMPLE 4

F108-2-pyridyl disulfide Coating of Porous Polystyrene Particles 20 mg dry porous PS particles with a size of 10 μm was incubated with 1.0 ml of ethanol. The suspension was mixed by end over end rotation for 2 hours at 25° C. After being settled down by centrifugation, porous PS particles were separated out by removing the ethanol and were then incubated in 1 ml of 0.2M phosphate-NaCl buffer. The PS particles were again centrifuged and were resuspended in 1 ml phosphate-NaCl buffer. After five consecutive washings, PS particles were incubated in 2.0 ml 4% F108-PDS solution. The solution was prepared by mixing Fl08-PDS in 0.2M phosphate-NaCl buffer and rotating end over end for 20 hours at 25° C. The coated beads were then washed eight times using the same phosphate-NaCl buffer above. The coating reaction is shown below;

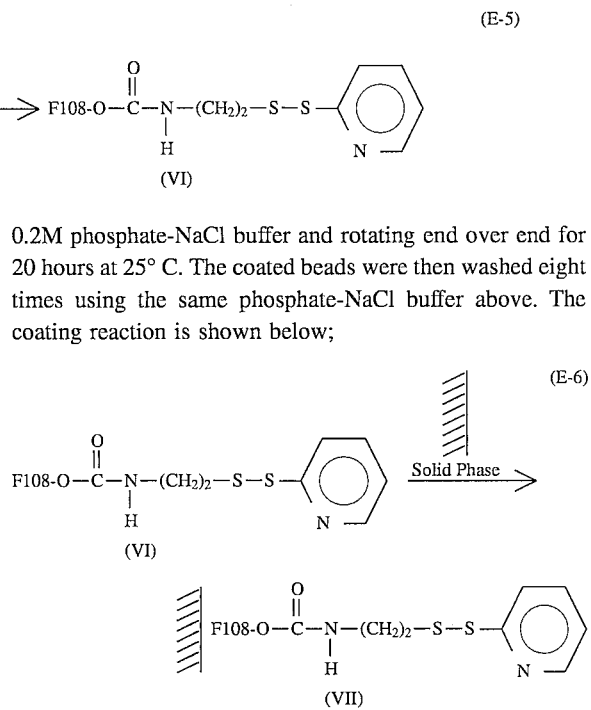

The amount of coated modified Pluronic F108 was determined by measuring the disulfide reactive groups. The coated PS particles were first incubated in 25 mM DTT for thiolation. After 10 minutes incubation, such coated particles were consolidated by centrifugation and the supernatant containing the released 2-thiopyridone was carefully transferred to a new centrifuge tube and was subjected to one more centrifugation to remove possible remaining particles. The 2-thiopyridone content was then determined photometrically as described above.

The weight of the PS particles, which have been trapped on a preweighed Millipore filter, was then determined after drying extensively over $P_2O_5$, and the content of reactive disulfide groups per dry weight of PS porous particles was then calculated from the disulfide group content and the 2-thiopyridone content.

EXAMPLE 5

Immobilization of β-galactosidase on Porous Polystyrene Coated with F108-2-Pyridyl Disulfide A protein was immobilized on the coated porous PS particles from Example 4. 11 mg β-galactosidase was dissolved in 1.0 ml 0.2M phosphate-NaCl solution containing 30 mM reduced glutathione. After 30 minutes reduction, the solution was passed through a PD-10 column equilibrated with phosphate-NaCl buffer, and 2.0 ml of β-galactosidase solution was collected, of which 1.0 ml was mixed with 0.5 ml suspension containing 10 mg F108-PDS coated porous particles (as in Example 4) and the other 1.0 ml was retained for thiol content determination.

In order to measure the amount of thiol groups, 0.2 ml of saturated solution of 2,2'-dithiopyridine in water (1.5 mM) was added to both the reference cuvette with 1 ml 0.2M phosphate-NaCl buffer and the sample cuvette with the above thiolated β-galactosidase. After 10 minutes incubation, the thiol concentration was calculated by measuring the concentration of released 2-thiopyridone as described above. The mixture of coated particles and β-galactosidase was rotated end over end for 48 hours at 4° C. and the particles were then washed with the 0.2M phosphate-NaCl buffer as described previously. The amount of immobilized β-galactosidase was determined by amino acid analysis.

Thiol-disulfide exchange is a specific and reversible reaction, and involves 2-pyridyl exchange reaction under release of 2-thiopyridone and formation of an stable aliphatic disulfide. The reaction occurs at both acidic and alkaline pH's and usually goes completely even if equal molar concentrations of reactants are used. When disulfide functional groups, designed to bind thiol-containing molecules, have is been immobilized on a solid phase, the bound molecules can be easily released and removed from the solid surface by adding low molecular weight thiol-containing reagents. The 2-pyridyl disulfide was thus substituted to Pluronic F108 by the reaction of para-nitrophenyl-carbonate activated F 108 and 2-(2-pyridyl dithio)ethylamine hydrochloride in the presence of TEA. F108 modified with the reactive disulfide (F 108-PDS) can be stably stored in solid form at room temperature in a desiccator over $P_2O_5$ for months. It is known that the 2-pyridyl disulfide group is very stable both in solid form and in aqueous solutions at physiological conditions of pH and temperature. The substitution of such reactive groups was only about 60%. Since the degree of substitution was calculated based on two active sites of the Pluronic molecule, this low value may indicate that about one disulfide active group was coupled to each F108 molecule.

By coating a modified Pluronic on a hydrophobic substrate the substrate surfaces become much more hydrophilic, and such coated surfaces have almost no nonspecific protein uptake upon the substrate surface. In this example β-galactosidase was used as the model protein and highly porous PS particles were the potential solid substrates for immobilization. The enzyme β-galactosidase from *E. coli* is one of the most extensively investigated of enzyme and is very popular for the preparation of enzyme immunoassays. These monodisperse PS particles (10 μm) used here provide extremely large surface area, approximately 350 $m^2/g$, and the advantage of easy sedimentation. By measuring the released 2-thiopyridone from the given amount of particles, the amount of adsorbed F108-PDS and the thiol content was determined. The results are shown in Table D, below. The immobilization of the protein is represented as follows;

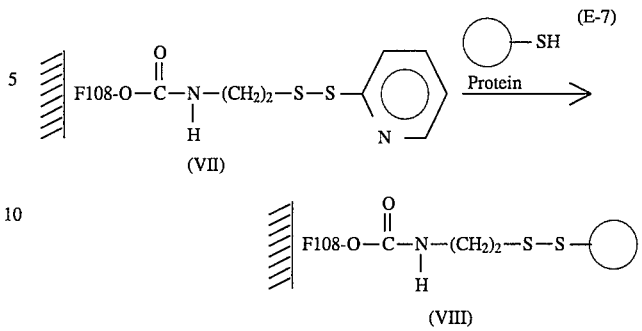

Adsorption of F108-PDS on other particles with similar hydrophobicity was measured and compared. The measured values of adsorbed amount per surface area shows that the adsorption properties are similar for these other hydrophobic particles and therefore the coating procedure is useful for other hydrophobic materials. Such hydrophobic materials include those hydrophobic polymers previously mentioned. PVAc is less hydrophobic than polystyrene and the adsorption of Pluronic and modified Pluronic surfactants on PVAc substrates is about half of that for polystyrene and other polymer substrates with similar hydrophobicity to polystyrene.

As a comparative test, the thiol-containing enzyme β-galactosidase was adsorbed on unmodified F108 coated porous PS particles. The adsorption was significantly lower than for the same PS particles that were coated by F108-PDS. These results are shown in Table D below;

TABLE D

Specific Binding of β-galactosidase on Porous Polystyrene Particles Coated with F108-2-Pyridyl Disulfide.

| | |
|---|---|
| Amount of bound F108-2-Pyridyl Disulfide (μmoles/g particle) | 45 |
| Thiol content of β-galactosidase (moles/mole protein) | 12 |
| Amount of bound β-galactosidase (mg protein/g particle) | |
| On particles coated with F108-2-pyridyl disulfide | 34 |
| On particles coated with unmodified F108 | <1 |

The above data demonstrates that β-galactosidase can be specifically immobilized on the particles through the thiol-disulfide exchange between F108-PDS and proteins. This shows the benefit of using modified Pluronic coatings according to the invention, as opposed to unmodified Pluronic without terminal reactive groups.

Other thiol proteins can be immobilized in a similar manner as β-galactosidase of this example. These include proteins that naturally contain thiol groups and proteins to which thiol groups have been introduced, such as γ-globulin.

EXAMPLE 6

Immobilization of thiolated anti IgE on Polystyrene Coated with F108-2-Pyridyl Disulfide F108-PDS adsorbed to the wells of PS microtiter plates was shown to bind a thiolated anti-IgE antibody. In a subsequent step, the IgE antigen was added to the wells in different amounts and allowed to bind specifically to the previously attached antibody. The amounts of bound IgE were subsequently determined through addition of anti-IgE, conjugated with an enzyme which permitted quantification (β-galactosidase). In a parallel experiment, the anti-IgE was added to uncoated wells of the PS microtiter plate and allowed to adsorb via "passive coating". The IgE antigen was then added in the same concentrations as were added to the F108-PDS modified wells, and the amounts bound were determined in the same way. The passive coating procedure represents the conventional way of performing an ELISA (enzyme linked immunosorbent assay). 1. The results are shown in Table E and the graph of FIG. 1.

TABLE E

Antigen binding of coatings

| KU IgE | Antigen bound by passive coating | Antigen bound via F108-PDS |
|---|---|---|
| 0 | 0.003 | 0.024 |
| 0.35 | 0.010 | 0.036 |
| 0.70 | 0.310 | 0.108 |
| 7.5 | 0.147 | 0.543 |

From results shown Table E and FIG. 1 it is clear that binding via passive coating results in a much weaker response to the antigen than binding via disulfide-exchange to the PDS moiety on adsorbed F108-PDS.

Because of its low adsorption of protein, an Pluronic coated surface will provide low background in protein quantification work. Typically, an ELISA test begins with the adsorption (to a PS microliter plate) of an antibody specific to the antigen of interest. The surface is then soaked with a solution of inconsequential protein which covers up remaining adsorption sites and reduces the risk of nonspecific adsorption of the enzyme-conjugated antibody added in the last step of the assay. As a model for these processes, PS microtiter plate wells were pre-exposed for 24 hours at 4° C. to either of: a) PBS (phosphate buffered saline), b) human plasma, c) BSA (bovine serum albumin, 100 mg/mL), d) F108 in PBS (2.2%) and e) F108-PDS in PBS (2.2%). The wells were subsequently well rinsed. To each of them was then added a solution of the enzyme β-galactosidase (0.1 mg/mL), which was allowed to adsorb for 24 hours at 4° C. Unadsorbed enzyme was then removed and discarded. After careful rinsing, the o-nitrophenyl β-galacto pyranoside (ONGP) substrate was added, and the color development was followed as a function of time. Visual color development was seen after 10 minutes in well a), after 30 minutes in well b), after 25 minutes in well c) and after more than 120 minutes in well d). Well e) with its ability to covalently attach the enzyme during the adsorption process, developed a strong color intensity within less than one minute.

This series of data clearly demonstrates the superior reduction in nonspecific adsorption caused by F108 (well d), as compared to the customary protein coating procedure (wells b and c). It also shows the F108-PDS analogue (well e) to be significantly more active than the passive coating (well a) in binding the enzyme to the surface.

This example illustrates the application of the F108-PDS coating to method to enhance the immunoaffinity of immobilized antibody by site-specific chemical coupling. Because of partial inactivation of antibody or the shielding of the antigen binding sites during the immobilization in prior-art adsorption or random coupling processes, immobilized antibody in these processes always has a low antigen binding capacity. In order to overcome these drawbacks, the orientation control of immobilization has been studied in many respects such as the improved specific binding by immobilizing Fab'-fragment and the importance of the chemical nature of solid phase to the antibody immobilization.

Comparative data indicates that antigen binding of the site specific immobilized antibody is eight times higher than that of passively coated antibody. Although other antibody of interest may not contain thiol groups, a number of techniques, e.g. modification through a nonessential amino group, have been used to thiolate antibodies and other molecules without changed activity or specificity. Thus, the coating by such Pluronic containing reactive disulfide groups becomes a general, yet very specific immobilization technique.

Regulating the Activity of the Adsorbed Surface

The content of adsorbed F108-PDS on the PS surface can be controlled by incubating solid phase to solutions of modified and unmodified Pluronic F 108 with different ratio of mixture. This approach can be used to design a suitable distance between immobilized biological molecules in order to give an optimal microenvironment for their biological function. It is generally very difficult to do such an adjustable distribution of the reactive molecules by direct chemical modification of hydrophobic materials.

In a series of tests, mixtures of F108-PDS and unmodified F108 of differing proportion were adsorbed on the surface of a PS latex substrate and the amount of active F108-PDS was measured. The results are summarized in Table F and the graph of FIG. 2.

TABLE F

Adsorption of Mixtures of Modified and Unmodified F108

| Proportion of F108-PDS (wt. %) | Amount of F108-PDS bound to particles (μ/moles/g) |
|---|---|
| 0 | 0 |
| 25 | 0.14 |
| 50 | 0.40 |
| 75 | 0.52 |
| 100 | 0.61 |

Figure 2:
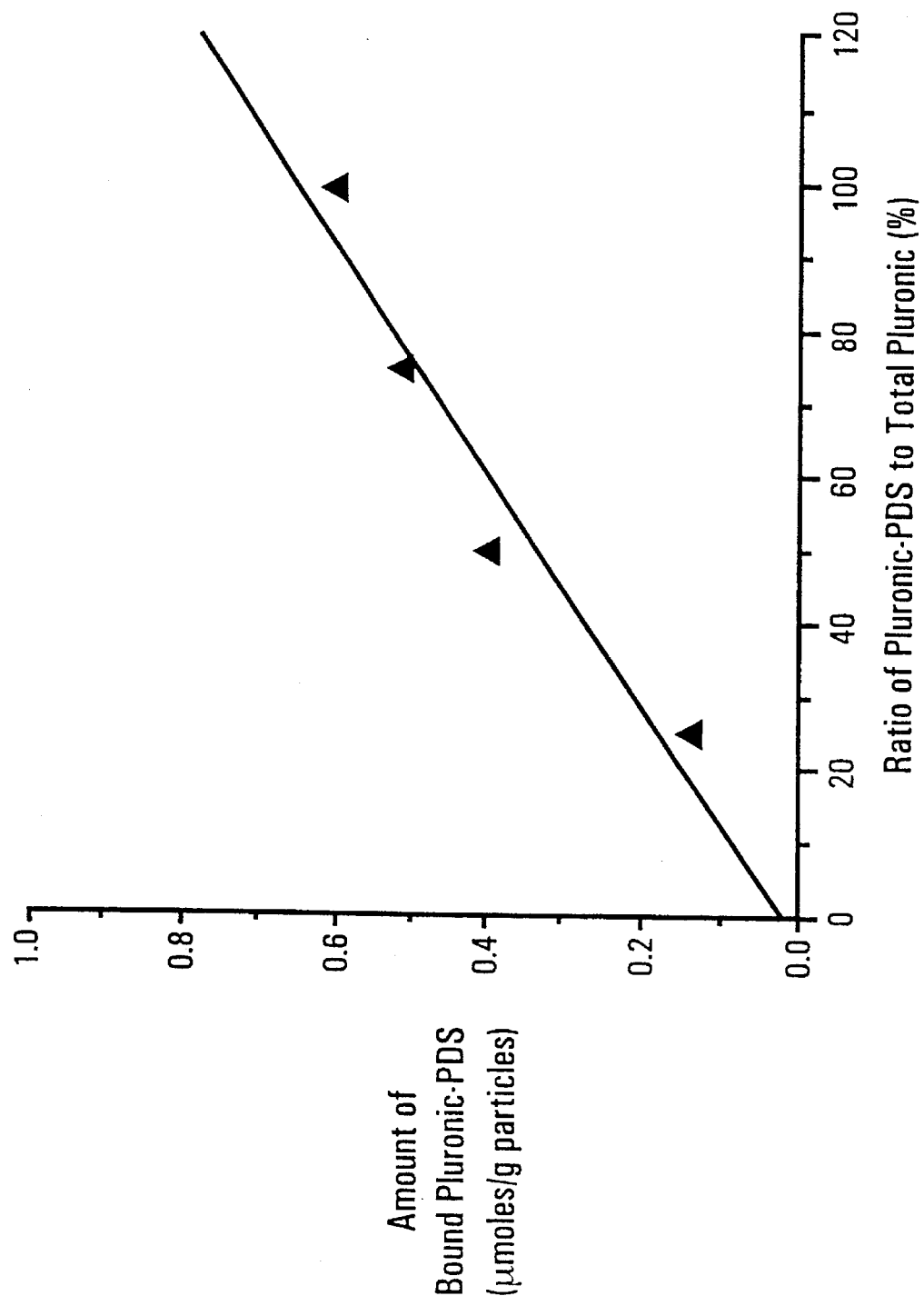
FIG. 2 is a graph showing activity of various adsorbed mixtures of activated Pluronic and non-activated Pluronic.

As shown in FIG. 2, the amount of activity is essentially directly proportional to the fraction of F108-PDS in the mixture. Accordingly, by regulating the proportion of modified Pluronic it is simple to predetermine the amount of activity on the adsorbed surface.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A method for forming a hydrophilic surface having a specific chemical reactivity on a hydrophobic substrate, which method comprises:
   (a) providing a hydrophobic substrate, the hydrophobic substrate characterized as having a surface water contact angle greater than about 60°,
   (b) providing a polymeric surfactant with substantially no reactivity to biopolymers, the surfactant characterized as having at least one pendant hydrophilic block (PEO) with one end attached directly or by bridging structures to a hydrophobic block (PPO) and the other end attached to pendant —O—H groups, the number of the pendant hydrophilic blocks (PEO) with attached —O—H groups (H—O—PEO) and the hydrophobic blocks (PPO) in the molecule being represented by:

e(H—O—PEO):b(PPO)

where b is an integer between 1 and 3, e is an integer between 1 and 6, and where PEO is the hydrophilic block and is of the formula:

—(—C$_2$H$_4$—O—)$_u$— where u is the same or different in each PEO block in the molecule and is greater than 50, where PPO is the hydrophobic block and is of the formula:

—(—C$_3$H$_6$—O—)$_v$— where v is the same or different in each PEO block in the molecule and is greater than 25, (c) reacting at least a portion of the —OH groups in the HO—PEO groups of the polymeric surfactant to provide reactive groups (R) on the pendant ends of at least a portion of the PEO groups to form a modified polymeric surfactant having pendant hydrophilic blocks (PEO) with one end attached to the hydrophobic block (PPO) and the other end attached to pendant reactive —O—R groups, R being stable in water and having the specific chemical reactivity that is provided to the surface, the number in the modified polymeric surfactant of the pendant hydrophilic blocks with attached —O—R groups (R—O—PEO—), and the pendant hydrophilic blocks with attached unreacted —O—H groups (HO—PEO—), and the hydrophobic block (PPO) in the molecule being represented by:

c (HO—PEO): d (R—O—PEO): b (PPO)

where b is an integer from 1 to 3, (c+d) is e, c is an integer between 0 and 5, and d is at least 1, and (d) adsorbing the PPO portions of the modified surfactant of step (c) upon the hydrophobic surface such that said PPO portions arc adsorbed upon the surface, and HO—PEO and R—O—PEO groups of the molecule extend from the surface.

2. The method of claim 1 wherein the bridging structures are chosen from the group consisting of —C$_2$H$_4$—, —C$_3$H$_6$—, and >N—CH$_2$—CH$_2$—N<.

3. The method of claim 1 wherein the polymeric surfactant in step (b) has the formula;

(H—(O—C$_2$H$_4$)$_u$—(O—C$_3$H$_6$)$_v$)$_2$N—CH$_2$—CH$_2$— N((—C$_3$H$_6$—O—)$_v$—(—C$_2$H$_4$—O—)$_u$—H)$_2$.

4. The method of claim 1 wherein the —OH groups in the HO—PEO groups of the polymeric surfactant in (b) are first reacted with a second reactant to provide reactive groups (R') on the pendant ends of at least a portion the PEO groups to form an intermediate having pendant hydrophilic blocks (PEO) with one end attached to the hydrophobic block (PPO) and the other end attached to pendant reactive —O—R' groups, where R' is chosen from the group consisting of;

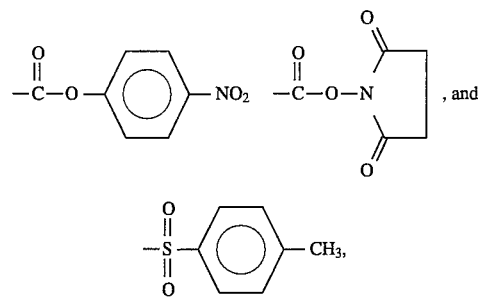

wherein the relative ratios in the intermediate molecule of the pendant hydrophilic blocks with attached reactive groups (R'—O—PEO), to the unreacted pendant hydrophilic blocks (HO—PEO), and to the hydrophobic block (PPO) being represent by the ratio;

c(HO—PEO):d(R'—O—PEO):b(PPO).

5. A method for forming on a hydrophobic substrate a hydrophilic surface having a predetermined density of specific chemical reactivity towards a thiolated protein, which method comprises:

(a) providing a hydrophobic substrate, the hydrophobic substrate characterized as having a surface water contact angle greater than about 60°, (b) providing a polymeric surfactant with substantially no reactivity to biopolymers, the surfactant characterized as having at least one pendant hydrophilic block (PEO) with one end attached directly or by bridging structures to a hydrophobic block (PPO) and the other end attached to pendant—O—H groups, the number of the pendant hydrophilic blocks (PEO) with attached —O—H groups (H—O—PEO) and the hydrophobic blocks (PPO) in the molecule being represented by:

e (H—O—PEO): b (PPO)

where b is an integer between 1 and 3, e is an integer between 1 and 6, and where PEO is the hydrophilic block and is of the formula:

—(—C$_2$H$_4$—O—)$_u$— where u is the same or different in each PEO block in the molecule and is greater than 50, where PPO is the hydrophobic block and is of the formula:

—(—C$_3$H$_6$—O—)$_v$— where v is the same or different in each PEO block in the molecule and is greater than 25, (c) reacting at least a portion of the —OH groups in the HO—PEO groups of the polymeric surfactant to provide reactive groups (R) on the pendant ends of at least a portion the PEO groups to form a modified polymeric surfactant having pendant hydrophilic blocks (PEO) with one end attached to the hydrophobic block (PPO) and the other end attached to pendant reactive —O—R groups, R containing a thiopyridyl group and being chosen from the group consisting of:

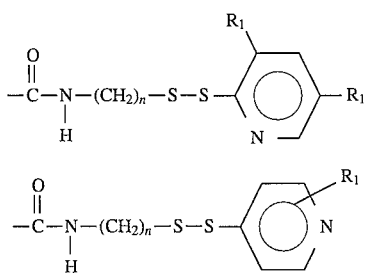

wherein n is greater than 1, preferably between 1 and 4, and $R_1$ is —$NO_2$ or —H, the number in the modified polymeric surfactant of the pendant hydrophilic block with attached —O—R groups (R—O—PEO—), and the pendant hydrophilic block with attached unreacted —O—H groups (HO—PEO—), and the hydrophobic block (PPO) in the molecule being represented by;

c (HO—PEO): d (R—O—PEO): b (PPO)

where b is an integer from 1 to 3, (c+d) is e, c is an integer between 0 and 5, and d is at least 1, and (d) adsorbing the PPO portions of the modified surfactant of step (c) upon the hydrophobic surface such that said PPO portions are adsorbed upon the surface, and HO—PEO and R—O—PEO groups of the molecule extend from the surface.

6. The method of claim 5 wherein in step (c) the PEO—OH groups are reacted with 4-nitrophenyl chloroformate to form an intermediate, which is then further reacted to form the thiopyridyl containing R groups.

7. The method of claim 5 wherein the density of the reactive sites on the surface is adjusted by mixing unreacted precursor from step (a) with the modified polymeric surfactant from step (c) at a predetermined ratio before adsorption in step (d).

8. The method of claim 1 wherein the —OH groups in the HO—PEO groups are first reacted to form an intermediate that is further reacted to form the modified polymeric surfactant having water-stable reactive groups.

9. The method of claim 1 wherein the —OH groups in the HO—PEO groups are first reacted with 4-nitrophenyl chloroformate to form an intermediate that is further reacted to form the modified polymeric surfactant having water-stable reactive groups.

10. The method of claim 9 wherein the reaction product of the polymeric surfactant and 4-nitrophenyl chloroformate is further reacted with reagent A to form the modified polymeric surfactant with water-stable reactive groups, reagent A having the formula:

$NH_2$—$(CH_2)_n$—S—S—R"

where R" is selected from the group consisting of (1) 2-benzothiazolyl, (2) 5-nitro-2-pyridyl, (3) 2-pyridyl, (4) 4-pyridyl, (5) 5-carboxy-2-pyridyl, and (6) the N-oxides of any of (2) to (5).

11. The method of claim 10 wherein reagent A is 2-(2-pyridyl dithio)ethylamine.

12. The method of claim 1 wherein the water contact angle of the hydrophobic substrate is greater than 70°.

13. The method of claim 1 wherein u is between 50 and 150 and v is between 25 and 75.

14. The method of claim 1 wherein u is between 80 and 130 and v is between 30 and 60.

15. The method of claim 1 wherein the polymeric surfactant has the formula

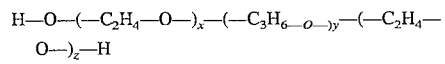

where y is between 25 and 75, x and z are the same or different, and x and z are between 50 and 150.

16. The method of claim 15 wherein y is between 30 and 60, x is the same as z, and x is between 80 and 130.

17. The method of claim 1 wherein b=1, c is 0 or 1, and d is 1 or 2, and e=2.

18. The method of claim 1 wherein b=1, c=0, d=1, and e=1.

19. The method of claim 1 wherein the portion of R that imparts the non-water reactivity to R in an aqueous environment is the structure

—S—S—R"

where R" is selected from the group consisting of (1) 2-benzothiazolyl, (2) 5-nitro-2-pyridyl, (3) 2-pyridyl, (5) 5-carboxy-2-pyridyl, and (6) the N-oxides of any of (2) to (5).

20. The method of claim 1 wherein the portion of R that imparts the non-water reactivity to R in an aqueous environment is chosen from the group consisting of hydrazino, thiopyridyl, tyrosyl, maleimide, 2-pyridyl disulphide, 5-nitro-2-pyridyl disulphide, 4-pyridyl disulphide, 5-carboxy-2-pyridyl disulphide, and the nitrogen oxides of 2-pyridyl disulphide, 5-nitro-2-pyridyl disulphide, 4-pyridyl disulphide, and 5-carboxy-2-pyridyl disulphide.

21. The method of claim 1 wherein R is:

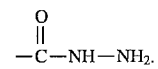

22. The method of claim 1 wherein R is:

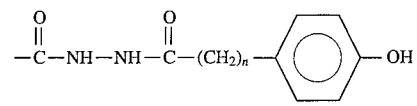

wherein n is between 1 and 4.

23. The method of claim 21 wherein R is chosen from the group consisting of:

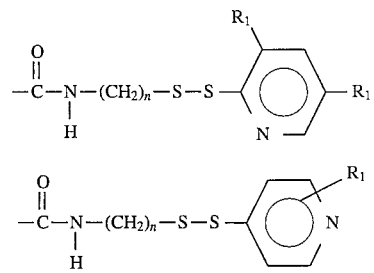

wherein n is greater than 1, and $R_1$ is —$NO_2$ or —H.

24. The method of claim 23 wherein n is between 1 and 4.

25. The method of claim 1 wherein R is:

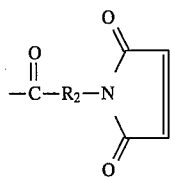

where $R_2$ is $-(CH_2)_n-$, a phenyl group or a cyclohexyl group, and n is greater than 1.

26. The method of claim 25 wherein n is between 1 and 4.

27. The method of claim 1 wherein the PEO content of the polymeric surfactant is between 10 weight percent and 80 weight percent.

28. The method of claim 1 wherein the PEO content of the polymeric surfactant is between 50 weight percent and 80 weight percent.

29. The method of claim 1 wherein the PEO content of the polymeric surfactant is between 70 weight percent and 80 weight percent.

* * * * *